US010817589B2

United States Patent
Lara et al.

(10) Patent No.: US 10,817,589 B2
(45) Date of Patent: Oct. 27, 2020

(54) SYSTEMS AND METHODS FOR IMPROVING PATIENT COMPLIANCE WITH A PRESCRIPTION DRUG REGIMEN

(71) Applicant: MicroHealth, Inc., New York, NY (US)

(72) Inventors: Marcos Lara, New York, NY (US); Miguel Lara, New York, NY (US); Raul Rodriguez-Esteban, Basel (CH); Alberto Lopez, Brooklyn, NY (US)

(73) Assignee: MICROHEALTH, INC., New York, NY (US)

( * ) Notice: Subject to any disclaimer, the term of this patent is extended or adjusted under 35 U.S.C. 154(b) by 732 days.

(21) Appl. No.: 14/664,615

(22) Filed: Mar. 20, 2015

(65) Prior Publication Data

US 2015/0193594 A1    Jul. 9, 2015

Related U.S. Application Data

(63) Continuation of application No. 11/611,799, filed on Dec. 15, 2006, now Pat. No. 9,015,054.

(60) Provisional application No. 60/751,256, filed on Dec. 17, 2005.

(51) Int. Cl.
| | |
|---|---|
| *G06Q 10/00* | (2012.01) |
| *G06Q 50/00* | (2012.01) |
| *G06F 19/00* | (2018.01) |
| *G06Q 50/24* | (2012.01) |
| *G09B 19/00* | (2006.01) |

(52) U.S. Cl.
CPC ........ *G06F 19/3456* (2013.01); *G06Q 50/24* (2013.01); *G09B 19/00* (2013.01)

(58) Field of Classification Search
CPC ............................ G06Q 50/24; G06F 19/3456
See application file for complete search history.

(56) References Cited

U.S. PATENT DOCUMENTS

| | | |
|---|---|---|
| 5,845,255 A | 12/1998 | Mayaud |
| 6,075,755 A | 6/2000 | Zarchan |
| 6,151,586 A | 11/2000 | Brown |

(Continued)

OTHER PUBLICATIONS

Menon-Johansson, A S., et al., "Texting decreases the time to treatment for genital *Chlamaydia trachomatis* infection," Sex Transm. Infect. 2006; 82:49-51, doi: 10.1136/sti.2004.014381.

(Continued)

*Primary Examiner* — Trang T Nguyen
(74) *Attorney, Agent, or Firm* — Orrick, Herrington & Sutcliffe, LLP

(57) ABSTRACT

A system for improving patient compliance with a prescription drug regimen is described. The system includes a patient database for storing patient information, the information including contact information for a patient communication device (such as a telephone, cell phone, computer, or PDA) along with a method for communicating with that device. The system further includes an alert database for storing information about prescription reminder alerts to be sent to patients. A send program running on a computer retrieves information about prescription reminder alerts from the alert database and transmits the prescription reminder alerts to a patient communications device over a communications network using the contact information and contact method stored in the patient database.

22 Claims, 13 Drawing Sheets

(56) References Cited

U.S. PATENT DOCUMENTS

| | | | |
|---|---|---|---|
| 6,161,095 A * | 12/2000 | Brown | G06F 19/3418 |
| | | | 705/2 |
| 6,168,563 B1 | 1/2001 | Brown | |
| 6,699,188 B2 | 3/2004 | Wessel | |
| 8,882,666 B1 * | 11/2014 | Goldberg | A61B 5/6838 |
| | | | 128/903 |
| 2002/0188503 A1 * | 12/2002 | Banerjee | G06Q 30/02 |
| | | | 705/14.23 |
| 2003/0018495 A1 | 1/2003 | Susssman | |
| 2004/0153339 A1 | 8/2004 | Hetzel | |
| 2004/0172447 A1 | 9/2004 | Miller | |
| 2004/0210458 A1 | 10/2004 | Evans et al. | |
| 2005/0187821 A1 * | 8/2005 | Lapsker | G06Q 30/02 |
| | | | 705/14.15 |
| 2005/0222875 A1 | 10/2005 | Lordeman et al. | |
| 2007/0280431 A1 * | 12/2007 | Alpsten | G06F 19/3418 |
| | | | 379/38 |

OTHER PUBLICATIONS

Gough, Neil, et al., "The Role of Mobile Phones in Increasing Accessibility and Efficiency in Healthcare," Moving the Debate Forward, The Vocalfone Policy Paper Series, No. 4, Mar. 2006.

Dunbar, Peter J., et al., "A Two-Way Messaging System to Enhance Antiretroviral Adherence," Jour. of Amer. Med. Informatics Assn., vol. 10, No. 1 Jan./Feb. 2003.

Vilella, Anna, et al., "The Role of Mobile Phones in Improving Vaccination Rates in Travelers," Preventive Medicine 38 (2004) 503-509.

Bielli, Emilia, et al., "A Wireless Health Outcomes Monitoring System (WHOMS): Development and Field Testing With Cancer Patients Using Mobile Phones," BMC Medical Informatics and Decision Making 2004, 4.

* cited by examiner

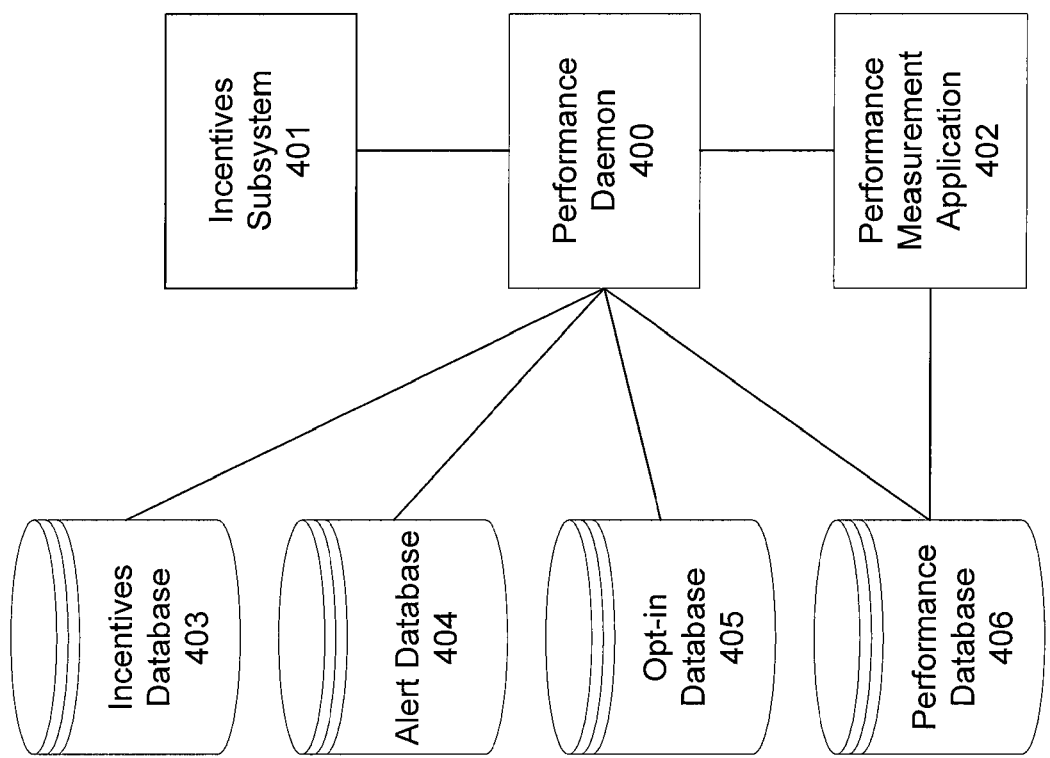

SYSTEMS AND METHODS FOR IMPROVING PATIENT COMPLIANCE WITH A PRESCRIPTION DRUG REGIMEN

CROSS-REFERENCE TO RELATED APPLICATIONS

This application is a continuation of co-pending United States application Ser. No. 11/611,799, filed on Dec. 15, 2006, which claims the benefit of U.S. Provisional Application Ser. No. 60/751,256, filed on Dec. 17, 2005. Priority to each of the prior applications is expressly claimed, and the disclosures of the applications are hereby incorporated herein by reference in their entireties and for all purposes.

FIELD OF THE INVENTION

The various embodiments disclosed below relate to computer systems and more specifically, computer systems configured to transmit prescription reminder alerts to patients through communications devices, including, but not limited to, wireless devices, handheld devices, telephones, and personal computers, reminding patients to adhere to a prescription drug regimen.

BACKGROUND OF THE INVENTION

Patient non-compliance, or the fact that patients do not take their medication as prescribed, is a major problem for the pharmaceutical industry and society as a whole. It is estimated that in the United States 125,000 people die each year due to problems associated with patient non-compliance, and the cost of non-compliance for the health care insurance industry is as high as $100 billion annually, including 10% of hospital admissions at a cost of $15.2 billion (2001) and 23% of nursing home admissions at a cost of $31.3 billion (2001). The United States economy is also impacted, as medication non-compliance leads to an estimated loss of 20 million work days annually (corresponding to $1.5 billion in lost revenue for employers).

In the United States alone, the costs of non-compliance for pharmaceutical manufacturers exceed $30 billion in annual lost revenue. Improving patient compliance with prescription drug regimens would benefit all the parties in the health care sector, from the patients themselves to other major stakeholders: Medicare/Medicaid and other Health Management Organizations (HMOs) would benefit from the savings related to the reduction in hospital and nursing home admissions; drug manufacturers and pharmacies would benefit from the associated increase in drug sales; Pharmacy Benefit Management (PBM) organizations would benefit from increased bargaining power due to increased sales, improved revenues, and improved services to patients and other stakeholders; patients would experience better service, higher satisfaction, and increased safety by increasing medication compliance.

Various systems have been devised in an attempt to overcome the causes of patient non-compliance, including simple forgetfulness of patients. These systems have included watches and other wearable devices, boxes of special design, and electronic medication dispensers. However, previous systems have proven to be workable only in controlled environments and they have failed to address a number of the causes of patient non-compliance. Prior art systems have failed to satisfy at least three requirements that must be met if a patient reminder system is to be workable in large commercial settings.

First, a system must provide tangible benefits to the sponsors who pay for the system. Performance data collected by the system should demonstrate the financial benefits to potential sponsors and thus justify sponsor participation in the system. Under certain circumstances, funds from sponsors could be used to make the service free for the patients, which will in turn stimulate patient participation in the system.

Second, the system must engage the patient. The advantage of using health-care providers to set up medications reminders has been noted in the prior art, for instance, research has demonstrated that 25-50% of patient non-compliance is derived from patient forgetfulness. However, prior art systems have lacked incentive systems to keep the patient engaged in the service over time. Additionally, many prior art systems, such as pager-based systems, have allowed limited or no patient participation.

Third, the system must have a practical implementation. Most compliance solutions offer an abstract approach to the patient non-compliance problem. However, they do not address a critical question: how to reach a critical mass in the highly fragmented health care market. Critical mass is required to make the method profitable and ensure its survival in the long run. A system that does not tackle the issue of how to create a critical mass of pharmacies and patients adopting the system cannot be implemented, and is functionally useless.

Prior art systems have failed to address the highly regulated nature of the health care industry, including regulation under the Health Insurance Portability and Accountability Act of 1996 (HIPAA). Health care systems deal with sensitive patient information, and errors by these systems can lead to serious liability for service providers. For example, a service failure could cause a patient to improperly take or miss doses of medication. Hackers who compromise the system could obtain sensitive patient information. Any system that operates in the health care industry must be reliable and secure; otherwise, the risk of liability will prevent its adoption. Patient consent is a necessary part of such systems, and there is a need to define an effective security protocol to protect the system against external attack. Examples of security procedures that are required to allow the method to operate in a commercial setting are: authentication, encryption, firewalls, back-ups, and data protection mechanisms and procedures in case of catastrophic events.

Prior art systems do not allow a reminder service to be transferred between pharmacy chains. Several pharmacy chains (e.g., Duane Reade) do not have terminals integrated to exchange patient data. This means that the service may not be transferable among pharmacy branches. As patients may change pharmacy chains, be restricted by health care network membership due to their insurance or for other reasons, or choose mail order pharmacies to fill certain prescriptions, it is important that a service be portable and transferable.

Patient reminder alerts are likely to be set up at a point in time different from the time the patient picks up the prescription. Thus, an activation mechanism must be in place to ensure that the alert system is activated at the right time, which would normally be defined by the prescription pick-up time. There is a need in the prior art to specify an activation mechanism that takes this delay into account.

Any commercially viable reminder system must also be designed to allow high load of information input, storage and output. In order to provide high availability, servers must be mirrored and databases must be replicated.

SUMMARY OF THE INVENTION

The various embodiments disclosed herein are generally directed towards providing alerts to patients to improve compliance with a prescription drug regimen. The present invention subscribes patients to the reminder system, sets up patient alerts, and transmits alerts to patient communication devices. These alerts are dispatched to the patient to remind the patient to take prescriptions on schedule and refill prescriptions, or to perform any other task related to their health care treatment.

The present invention includes a patient database for storing patient information and an alert database for storing prescription reminder alerts. A send program queries the alert database and sends the prescription reminder alerts to patients at a determinable time. According to some embodiments of the present invention, an incentives database may store incentives definitions which define events, the occurrence of which will trigger the rewarding of incentives to patients. An incentives program will receive notification of those events and send appropriate incentive verification messages. According to some embodiments of the present invention, a performance database will store information about alerts that have been sent and feedback messages that have been received along with other information usable to measure the performance of the prescription reminder system. A performance measurement program may query the performance database, perform analyses on the results of those queries, and generate reports based on those analyses.

According to some embodiments of the present invention, an incentive system is available which refunds part of the savings to the patients as an incentive to participate in the system and comply with treatment regimens.

According to some embodiments of the present invention, a performance subsystem is available allowing the measurement of the tangible benefits of the system to various parties, including increases in sales, savings in health care costs, and improved patient satisfaction. Quantifying the financial benefits of the system may provide data to raise funds from sponsors, thus increasing the chance that the system is adopted.

According to some embodiments of the present invention the system may be interactive such that the patient can provide feedback, access his or her profile online, check for incentives, opt-out of the service, or receive additional health care information related to his or her disease.

According to some embodiments of the present invention, the system detects when medications are going to be taken at the same time or close to one another. In such cases, it can provide the option of combining some or all of the messages associated with these prescriptions or, either locally or remotely, it can automatically merge all or part of the messages in order to reduce the number of messages that must be sent to the patient.

According to some embodiments of the present invention, the system allows the point of service to quickly and efficiently set up known drug regimens. The system can include templates as a time-savings device during alert setup. The system may also be programmed to use e-Rx information or bar-code information to speed setup.

According to some embodiments of the present invention, the system includes a computer-based security mechanism that will minimize liability risk for the service providers, notifying service providers of risk and not allowing alerts to be sent if unsafe conditions are detected.

According to some embodiments of the present invention, the system allows service transferability from any dispensing point nationwide to another (e.g., from Walgreens to CVS, or to mail order pharmacy).

PARTICIPANTS

The patient is the individual who is subject to the drug regimen and who receives reminders from the system.

The sponsor pays, in whole or in part, for the reminder service, maintenance, or incentives offered to a certain patient group. Numerous organizations may be sponsors, including pharmacies, drug companies, insurance companies, or pharmacy benefit managers. Any organization that stands to benefit financially from the reminder service may decide to become a sponsor.

The point of service is where a patient interacts with the alert system, such as a pharmacy, a primary care physician, a cell phone, or a web site. Pharmacies are ideally situated as points of service, because they know when drugs have been picked up and can thus automatically activate the reminder system at that time. Physicians are another possible point of service, but because they do not know when prescriptions have been picked up, they may not be able to activate the service automatically.

The service provider manages the operation of the alert system and provides the alert message to patients. Pharmacy Benefit Managers are in a unique position to operate as a service provider. Pharmacy Benefit Managers are ideal for offering the service to pharmacies, collecting patient information, measuring the performance of the system, and providing mail order services. Three Pharmacy Benefit Managers manage more than 50% of the prescriptions in the United States and the majority of mail order pharmacy prescriptions in the Unites States. With only one large Pharmacy Benefit Manager offering the service, the service will obtain the critical mass needed to be practical.

BRIEF DESCRIPTION OF THE DRAWINGS

In order to better appreciate how the above-recited and other advantages and objects of the present inventions disclosed herein are obtained a more particular description of the present inventions briefly described above will be rendered by reference to specific embodiments thereof, which are illustrated in the accompanying drawings. Understanding that these drawings depict only typical embodiments of the invention and are not therefore to be considered limited of its scope, the invention will be described and explained with additional specificity and detail through the use of the accompanying drawings in which:

FIG. 4 illustrates the operation of the performance measurement system in accordance with one embodiment of the present invention.

DETAILED DESCRIPTION OF THE DRAWINGS

The foregoing description and figures are focused on wireless alerts. However, the system is not limited to wireless alerts and may also be able to download information directly to a patient device at the point of service, with or without the alert activation coupled to the information download. In addition, reminders may be provided on other channels such as email, automated phone calls, or multimedia messaging. The system may also be used to improve the quality of veterinary care of animals.

Figure 1A:
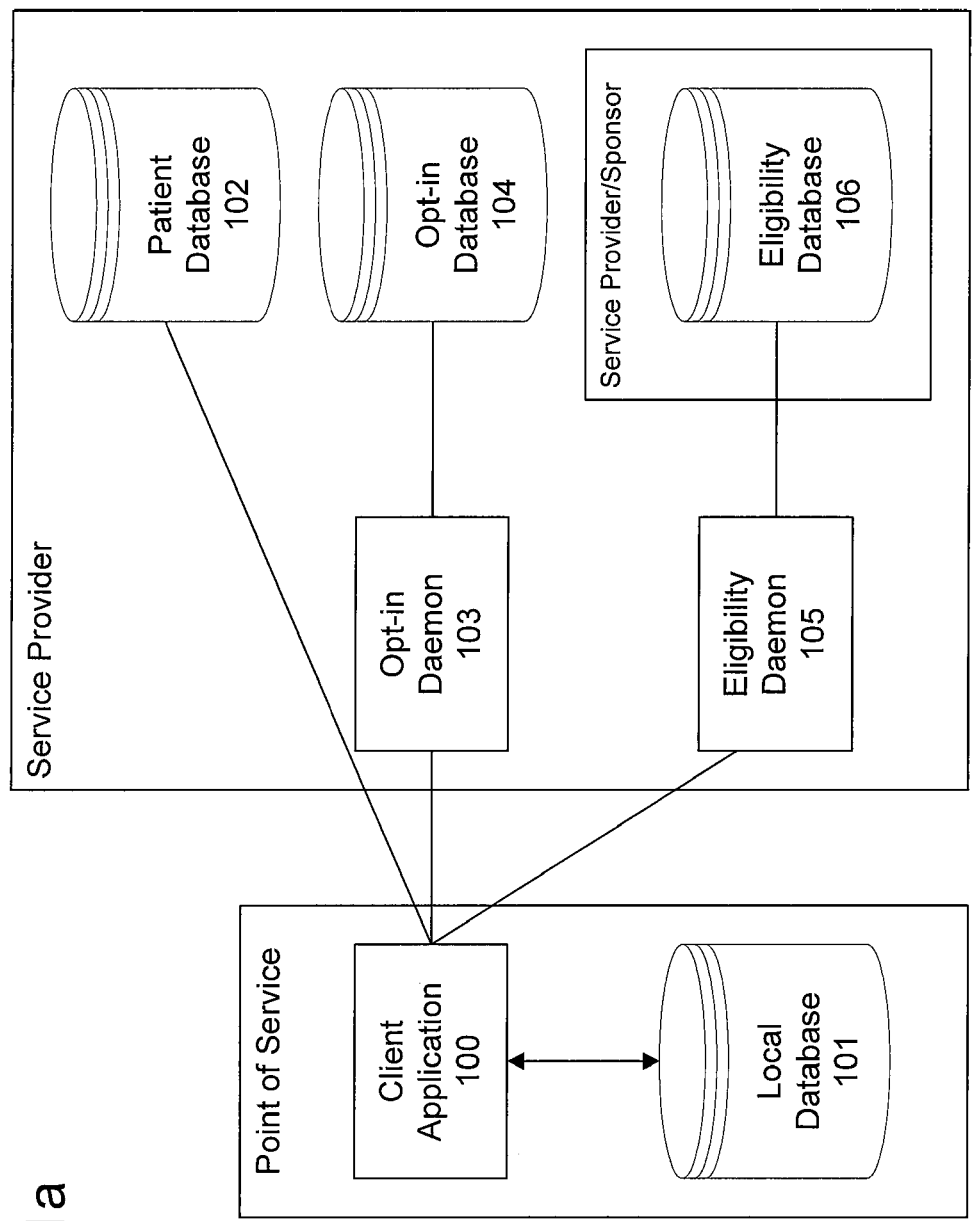
FIGS. 1a and 1b illustrate the operation of the subsystem for subscribing patients and determining whether patients are eligible for sponsorship in accordance with one embodiment of the present invention.
Figure 1B:
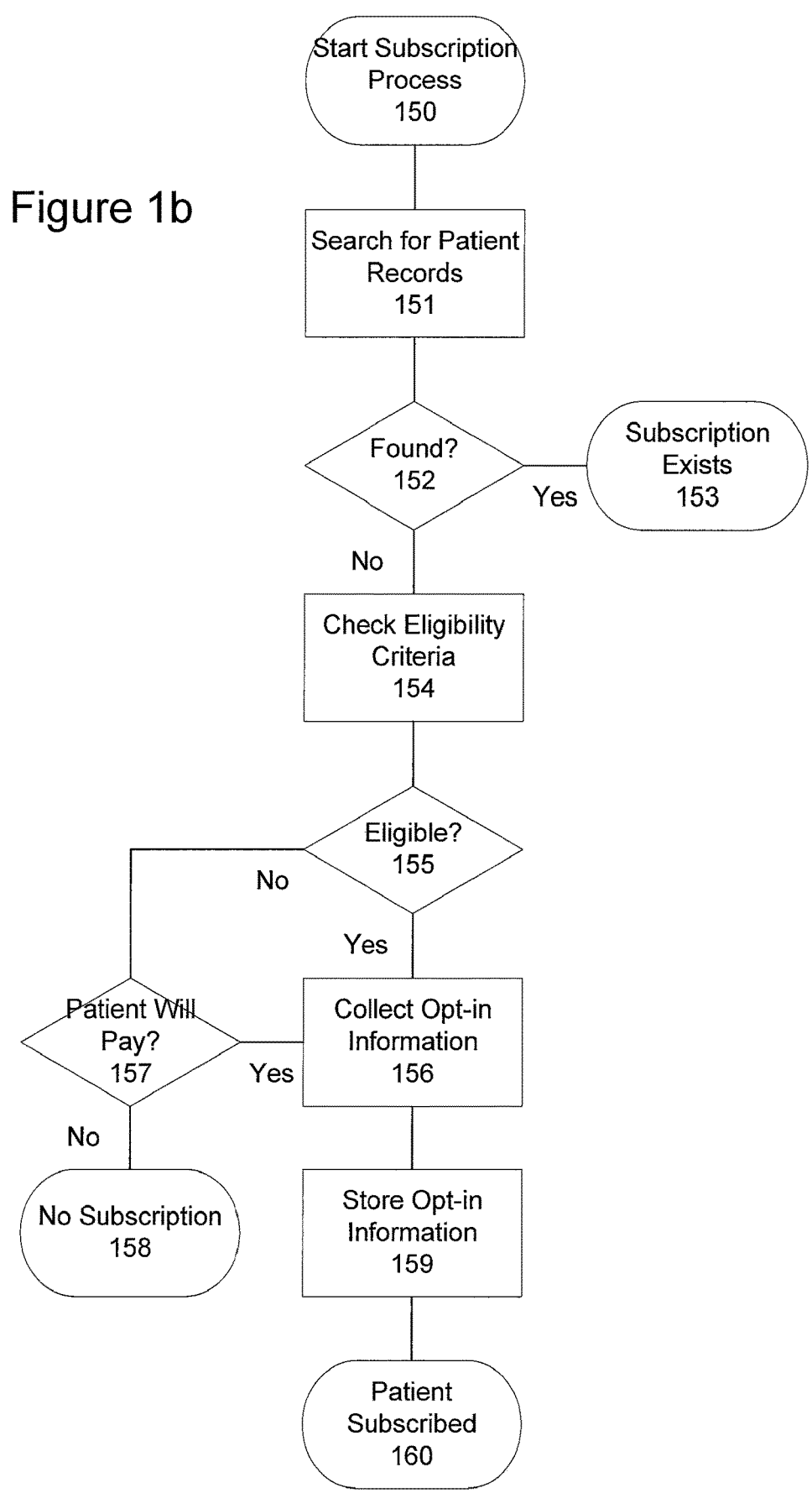

FIGS. 1a and 1b illustrate the operation of the subsystem for subscribing patients including determining whether patients are eligible for sponsorship in accordance with one embodiment of the present invention.

Referring to FIG. 1b, the subscription process begins at step 150, when the patient purchases a prescription at a point of service, such as at a pharmacy. The point of service employs a Client Application 100 to interact with the alert system and subscribe the patient to the service. The Client Application 100 may be a standalone application or an add-on to a commercial product. The Client Application 100 may run on a terminal or a computer with a display and input means such as a keyboard and mouse. The terminal may be connected to a communications network which allows the point of service to transmit information to and receive information from the service provider and other entities involved in the system.

In step 151, the point of checks to see if the patient's alert preferences, prescription history, and other pertinent data have already been stored either locally in the Local Database 101 or at the service provider in the Patient Database 102. If patient information is found in decision block 152, the patient is already subscribed in the system and no further processing is necessary, the process terminates at step 153 with a determination that a subscription exists, and a new alert may be set up for the patient.

If the patient has not yet subscribed to the alert system, patient information will not be found at decision block 152, and the point of service must collect information about the patient, including where to send alerts (e.g., a cell phone number or email address) as well as other alert preferences, such as whether the patient wishes to receive health education updates. Other information may include the patient's Social Security Number, insurance information, medical records, the patient's risk profile, eligibility criteria, or specific information related to performance studies the patient is participating in. Some of this information may be collected at time of enrollment, and some may be added later in conjunction with setting up certain reminders or in association with other events. It is also possible that the point of service, service provider, or other participants will already have much of this information based on its dealings with the patient. Referring to FIG. 1a, this information will be stored in the Local Database 101 as well as in the Patient Database 102.

The point of service must then check patient eligibility for sponsorship in step 154. Criteria for eligibility may include a patient's insurance carrier, patient demographics, or prescription information. The criteria may be stored in an Eligibility Database 106 at the point of service, at the service provider, or at a sponsor organization, such as a health maintenance organization, pharmacy benefit manager, drug company, or insurance company. The Eligibility Daemon 105 will receive an eligibility query and will check, at decision block 155, to see if a particular patient is eligible by searching in the Eligibility Database 106. Sponsorships may be offered by the patient's health insurer, pharmacy benefit manager, drug companies, drug manufacturer, or the pharmacy. If the patient is not eligible to receive sponsored service, the patient may choose to pay for the service instead at decision block 157. The point of service must also obtain authorization (opt-in) information from the patient in order to complete a subscription in step 156. Because of the highly regulated nature of the health care sector, and the possible liability associated with service failure, it is necessary to obtain specific permission from the patient to be enrolled in the reminder service. Opt-in will include informed consent by the patient to participate in the reminder system, notification about the possible consequences of doing so, and a waiver of liability for patient misuse of the reminder system. The opt-in may also include privacy notices and any other notices regarding studies the patient may elect to participate in. If the opt-in information is collected electronically, it is stored locally and sent to the service provider. The Opt-in Daemon 103 at the service provider receives the opt-in information and stores it in the Opt-in Database 104. If it is collected on paper (i.e., the patient signs an opt-in form) a copy of the information is kept locally and a copy is sent to the service provider (either mailed or scanned and sent electronically) where it is stored in the Opt-in Database 104. The opt-in must be obtained during initial enrollment and checked every time a new alert is set up in order to mitigate liability risks as shown in steps 155-160.

Once this process has been completed, a patient has been subscribed for the alert service and the point of service can create alerts for the patient. Additionally, because the patient has been enrolled with a particular service provider, the reminder service may be used by other points of service than the one where the patient enrolled. New points of service may require the patient to repeat some or all of the steps above, such as opt-in, verification, and eligibility checking in order to use the service at that location.

FIGS. 2a through 2d illustrate the operation of the subsystem for setting up, modifying, and transmitting alerts, according to one embodiment of the present invention. The Point of Service Database 202 stores information about the various points of service 200 registered with the system. The Point of Service Database 202 includes a unique identifier for each point of service (POS_ID), a name for the point of service (POS_NAME), and a password for the point of service (POS_PASSWD). A point of service must log in to the reminder system in order to set up alerts. The Point of Service Database 202 may also include information useful to the service provider, such as billing, address, and contact information.

The Patient Database 203 includes information about each patient registered with the system. The Patient Database 203 stores information about each patient registered with the system, including the patient's Social Security Number and information about how to contact the patient, such as a cellular number (for SMS or telephone communication), telephone number, or email address. The Patient Database 203 may also include other information about the patient such as compliance rate, health provider, or incentive or performance data.

The Opt-in Database 204, as described above, stores opt-in information for each patient that is subscribed to use the system. This information confirms that the patient has consented to receive alerts and has waived any potential liability.

The Alert Database 205 includes information about each alert that will be sent by the system. The Alert Database 205 includes a unique identifier for each alert (ALERT_ID), the destination of the alert (ALERT_DEST), the alert message (ALERT_MSG), the delivery schedule for the alert (ALERT_SCHEDULE), and the point of service associated with the alert (POS_ID). The Alert Database 205 may also include alternative means for contacting the patient, a patient identifier, prescription information, or health insurance information.

The Log Database 206 stores information about what operations the system has conducted for billing, auditing, or other purposes.

Figure 2A:
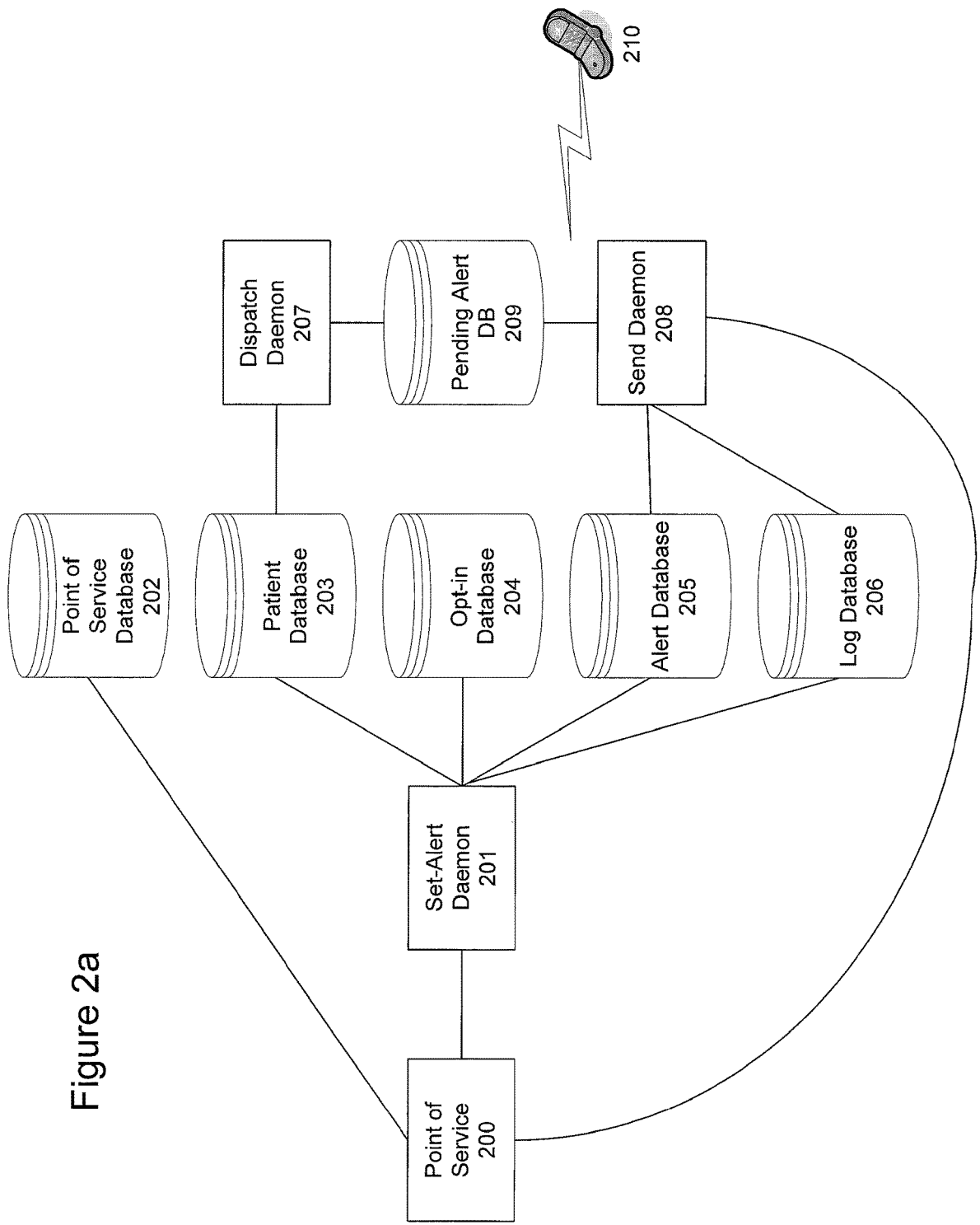
FIGS. 2a through 2d illustrate the operation of the subsystem for setting up, modifying, and transmitting alerts, according to one embodiment of the present invention.
Figure 2B:
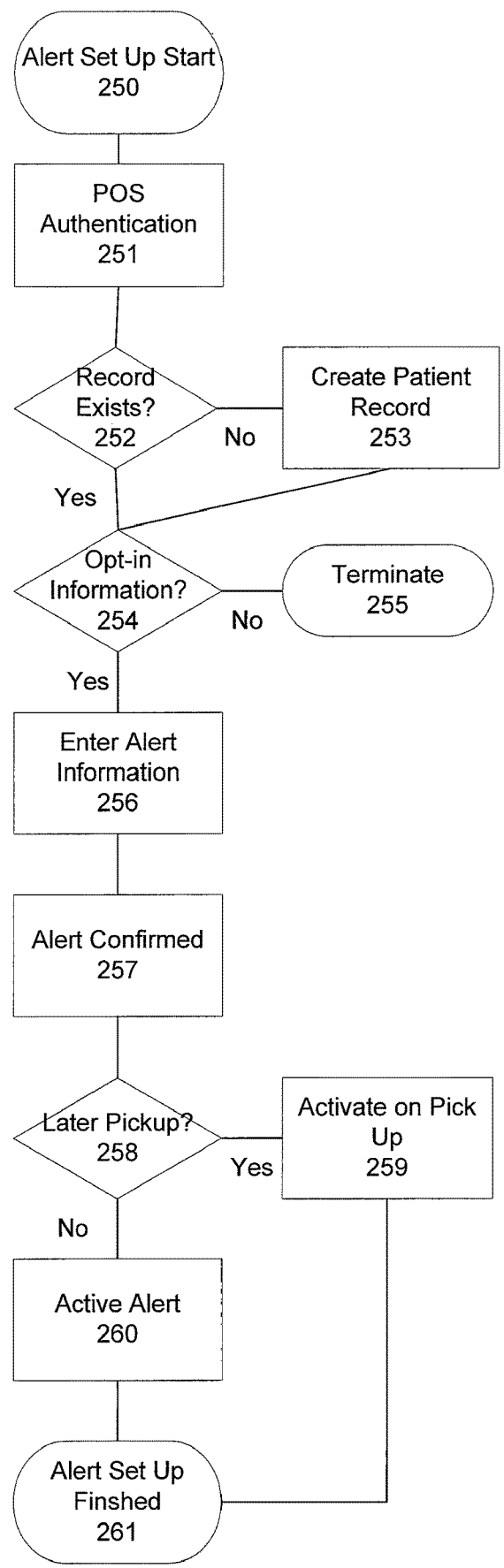

Referring to FIG. 2b, to set up an alert, an operator at the point of service must log in to the system in POS Authentication step 251. During log in, the operator must present credentials matching a registered point of service in the Point of Service Database.

Once the point of service has logged in, the system checks to see if the patient for which the alert is being created already exists in the Patient Database at decision block 252. If not, an entry for the patient's information is created and the information is entered into the database in step 253. The system must also check the Opt-in Database to verify that the patient has elected to receive reminders at decision block 254. If a proper entry is not found in the Opt-in Database, that information must be supplied, or the system will not permit alerts to be set for that patient and will terminate at 255.

Once the patient and opt-in information has been confirmed, the system will set up an alert in the Alert Database. The information needed for the alert may be automatically extracted from the prescription information, such as by connecting to the automatic barcode reader, or it may be manually entered by an operator at the point of service in step 256. The prescription information may include prescribing physician, specific information about the drug regimen, and recommendations for the patient, either generic or tailored to the patient. The Set-Alert Daemon 201 processes the alert information and stores it in a suitable format in the Alert Database 205. For instance, a single prescription may generate multiple reminders which will correspond to multiple entries in the Alert Database 205.

The reminder system may also include a set of templates to aid the operator at the point of service in quickly setting up the proper reminders for known drug regimens. The system may also allow the operator to combine reminder messages if the patient will be taking several drugs in order to reduce the number of reminder messages received by the patient.

In step 257, the service provider will confirm to the point of service when the alert has been set up. If the patient must return at a later date to retrieve the prescription at decision block 258, the alert will not be activated until the patient returns and picks up the prescription in step 259. This can be done by coupling the activation to the purchase of the prescription or by manually activating the prescription. If the prescription is picked up immediately, the alert is activated in step 260. The application that bills the prescription may activate the local alert application with the parameters that identify the prescription. The process could also be performed manually at the point of service or by the patient, such as by calling a particular phone number, sending a text message to a particular number or logging into a website.

Alert information is transmitted to the service provider in an alert message comprising a number of fields describing the alert characteristics: the name of the medicine, the doctor, the times and dosages for taking the prescription, the number of refills, additional medical advice and other options such as if the patient wants to receive general health care advise. This alert message is received by the Set-Alert Daemon 201 in the service provider, which is an application generally polling one of the ports of the network memory space of a computer. The Set-Alert Daemon 201 parses the incoming messages and stores it in the Alert Database 205.

Figure 2C:
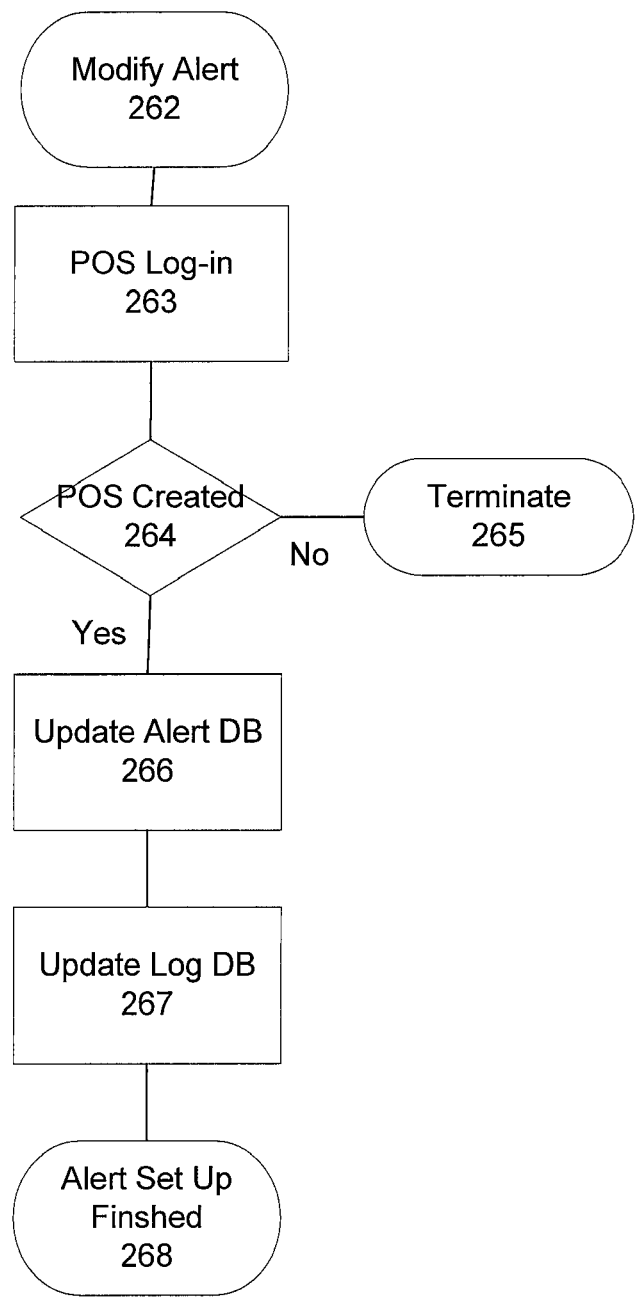

Referring to FIG. 2c, the system also permits a point of service 200 to alter alerts it has already created. To modify an alert, a point of service must first authenticate itself to the service provider in step 263, as described above in connection with the creation of an alert.

Once logged in, the point of service may request the modification or deletion of any alert in the Alert Database 205. The system must first verify that the specified alert was created by this point of service by checking the POS_ID field of the alert to be modified in step 264. If the point of service is authorized to change the alert, the Set-Alert Daemon 201 will process the request and modify or delete the corresponding entries in the Alert Database 205 in step 266. Finally, the modification or deletion is recorded in the Log Database 206, for auditing or billing purposes in step 267.

Figure 2D:
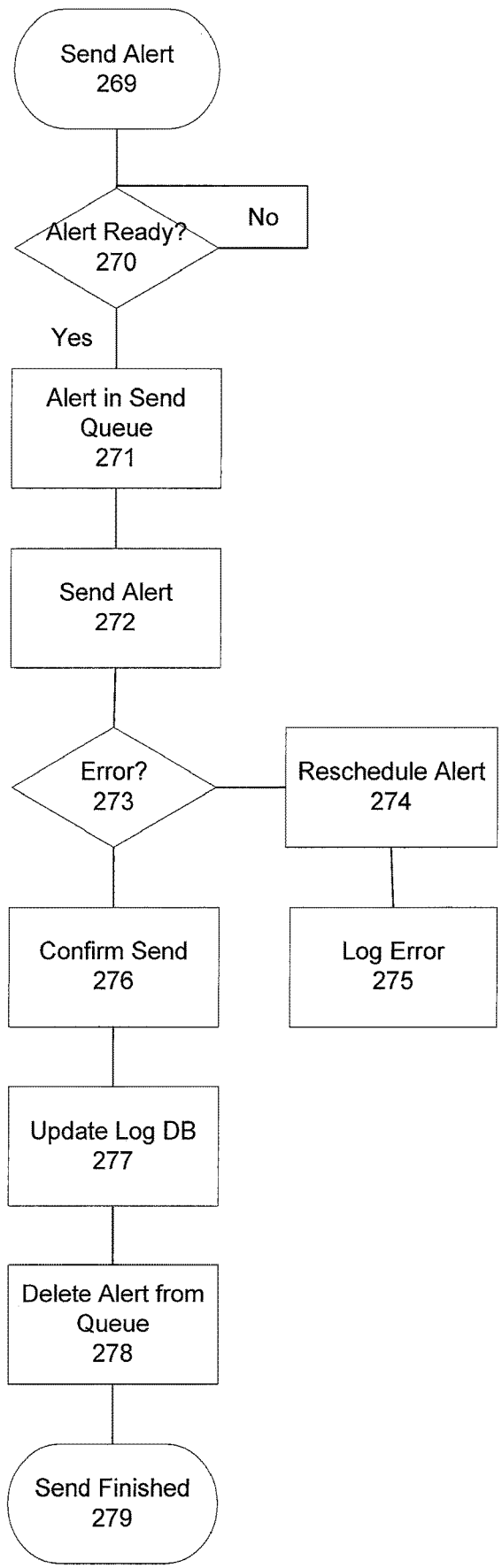

Referring to FIG. 2d, once the alert is established in the Alert Database 205, the Dispatch Daemon 207 checks periodically to see what alerts need to be sent in decision block 270. When an alert is due, the Dispatch Daemon 207 places the alert in a queue to be processed by the Send Daemon 208 in step 271. The Send Daemon 208 interfaces with one or more telecommunication service providers and sends the alert in an appropriate form (e.g., an email or text message) in step 272. The system communicates with a telecommunications service provider via protocols such as TCP/IP, MMS/SMS, or SMTP. The connection to the communication provider may be through any number of physical media, including ADSL, ISDN, cable modem, or frame relay.

If there is no error in sending the message at decision block 273, delivery of an alert may be confirmed by the telecommunication service provider in step 276. When confirmed, the Send Daemon 208 will update the Log Database 206 in step 277 (e.g., for billing purposes) and delete the alert from the Alert Database 205 in step 278. In the case of an error at decision block 273, the Send Daemon 208 will mark the alert as faulty, cause the Dispatch Daemon 207 to try again later in step 274 (e.g., by rescheduling the alert for 10 minutes later), and log the event in step 275. Eventually the alert will reach the patient, and a confirmation of receipt may also be sent to the point of service 200.

In accordance with one embodiment of the present invention, the system may be designed to handle high traffic load. The Alert Database 205 may be replicated and load balanced and multiple Send Daemons 208 may be used to simultaneously handle reminder transmissions. Each instance of the Alert Database 205 may be serviced by a different Dispatch Daemon 207 and each of these Dispatch Daemons 207 may place pending alerts in a Pending Alert Database 209. The multiple Send Daemons 208 may then retrieve messages from the Pending Alert Database 209 and send them to one or more telecommunications providers 210 in parallel.

Figure 3A:
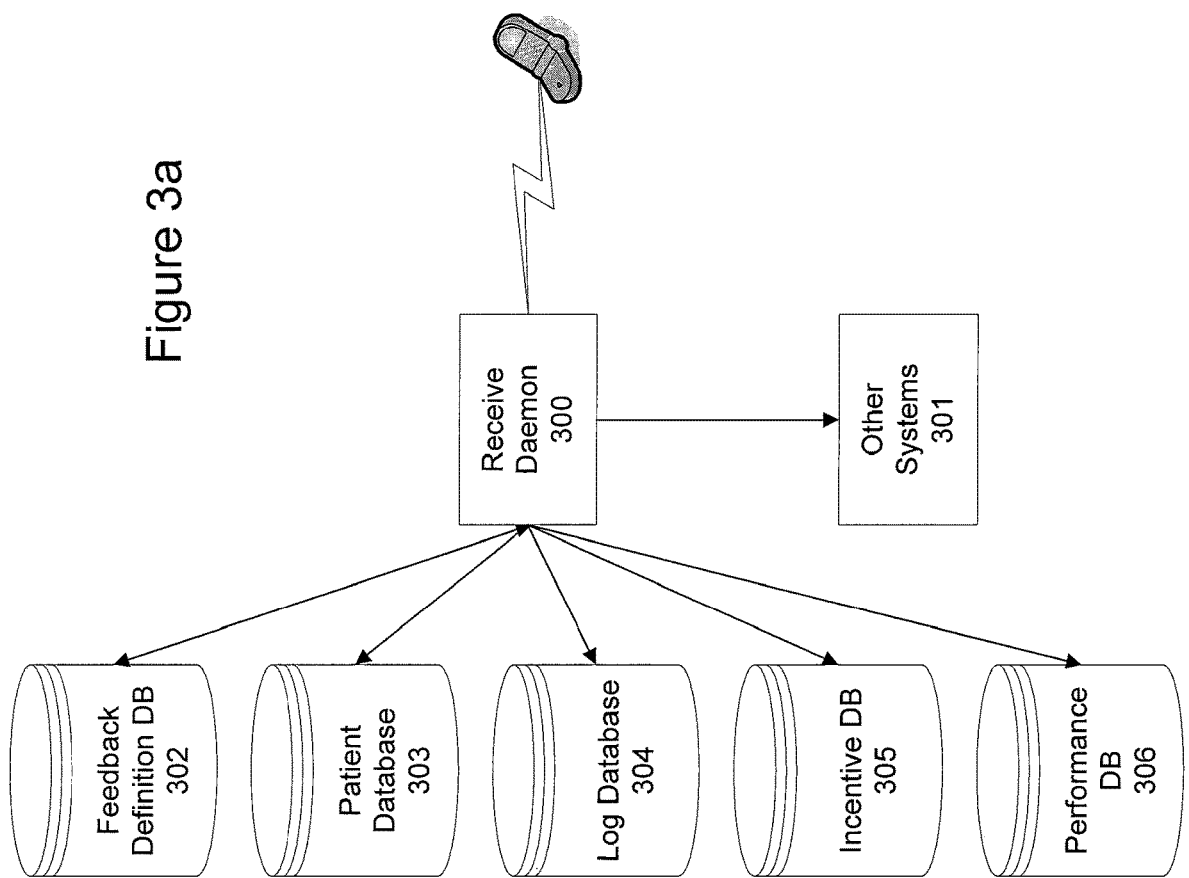
FIGS. 3a and 3b illustrate the process for patients to provide feedback in accordance with one embodiment of the present invention.
Figure 3B:
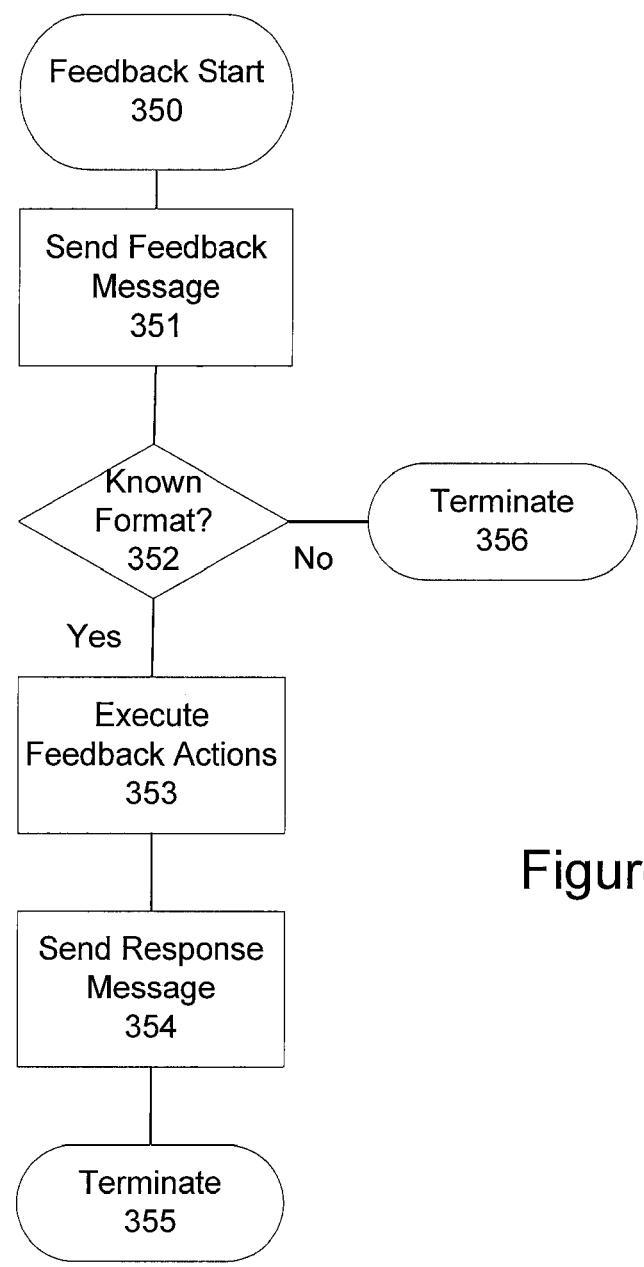

FIGS. 3a and 3b illustrate the process for patients to provide feedback in accordance with one embodiment of the present invention.

The alert system can receive feedback information from the patient. The patient may independently send a feedback message or the patient may send a feedback message in response to an alert. The Receive Daemon 300 receives all feedback messages from the patient. The Receive Daemon 300 stores any feedback messages in the Log Database 304. A patient feedback message may also trigger an update of the information in the Patient Database 303, for example, to update compliance information in the Patient Database 303 when the patient replies to an alert with a confirmation of compliance. Referring to FIG. 3b, when the system receives a feedback message sent from a patient in step 351, the system checks the message format in the Feedback Definition Database 302. If the message format is correct at decision block 352, the system will interpret the query and trigger the corresponding actions in step 353. These actions may be logged in the Log Database 304 in step 354 and may also generate information for the Incentive 305 or Performance 306 Databases. For example the user may send the message "ALERT OFF," requesting temporary deactivation of the alert system. In this case the Receive Daemon 300 would check in the Feedback Definition Database 302 for messages of the form "ALERT ON/OFF" and would interpret the query and trigger the subsequent actions, such as logging, deactivation of the alerts or communication with external subsystems such as the incentive or performance engines. The system may also respond to feedback messages in step 354 by sending response messages to the patient. These responses may be handled as regular outgoing alerts or by other means after processing of the feedback message. The system may have certain feedback messages parameterized so that pre-configured responses are sent to the patients.

FIG. 4 illustrates the operation of the performance measurement system in accordance with one embodiment of the present invention.

Patients are informed in the opt-in forms of the use of the alert system for the purpose of improving their health and the general well-being of the population at large. This includes the use of alert statistics to track compliance and to follow-up on the patients' fidelity to the system (e.g., fill, refill, feedback, coupons, other). The system stores opt-in information for each patient in the Opt-in Database 405. Opt-in information is sent either with paper records, electronic signatures, or other methods of validation. Current alerts information is stored in the Alert Database 404. Since this database stores only active alerts is necessary to keep track of the alert history of a particular patient in order to conduct performance studies related to that patient. This can be done by the Performance Daemon 400. The Performance Daemon 400 regularly queries the Alert Database 404 and collects information about a selected set of patients. The importance of regular polling comes from the fact that alerts may be changed either by the patients or other users that are authorized such as the point of service, and the service provider. The Performance Daemon 400 ensures changes to the alert data recorded by regularly querying the Alerts Database 404 and updating information in the Performance Database 406.

Selected information from the Alert Database 404 and Opt-in Databases 405 is stored in the Performance Database 406 in a set of tables. One table contains the patients for whom performance is being measured. The database may include a field called PATIENT_ID as well as other fields storing other information about the patient. A second table contains alert and opt-in information for each patient being monitored by the performance system. This table could include fields such as PATIENT_ID, DAY_SET, LOCATION, MEDICINE, and DOCTOR.

Finally, a set of tables representing lists of patients in different studies could be optionally included. These tables would each represent a specific performance study that is being carried out. Another important component for performance studies would be the Incentives Database 403. The Incentives Database 403 includes information about specific incentives given to patients and in which dates and in which terms.

A Performance Measurement Application 402 can run queries over the data stored in the Performance Database 406 and other databases of the system. It can generate reports containing alert, incentive, and opt-in information about groups of patients under study. These reports can be compared to control groups in comparative studies.

The system can also send alert messages to patients requesting demographic data. The alert would explain the reason for collecting the data, and if the patients provide a response, it can be stored in the Alert Database 404. The Performance Daemon 400 would gather this data during its queries of the Alert Database 404 and store it in the Performance Database 406.

The performance measurement system may incorporate data from numerous sources including health care institutions like PBMs, which receive the reimbursement claims for one patient regardless of the pharmacy or hospital the patient is treated; information coming from HMOs, physician (e-prescriptions, etc), Medicaid/Medicare, or other parties could be used as sources if their information meet certain requirements. If historic patient information is available, it can be used to compare patients pre and post intervention. Otherwise, a record of fill and refill information will be created as the patient obtains new prescriptions. Data may come directly from the point of sale or dispensation, from the patient, or from an existing database that previously stored the required information such as a PBM database.

The performance measurement application may perform various analyses on the available data and may compare data between a study group using the reminder service and a control group that is not. For instance, the performance measurement system could collect information relevant to the study (such as the frequency of fill, refill or satisfaction level) of two or more cohorts with a certain disease or demographic profile. The first cohort (intervention) could be subscribed to the reminder service. The second cohort (control), are either patients not subscribed to the program or the same intervention group prior to enrolling to the reminder service.

The performance measurement application could then compare control and intervention groups to find statistical differences in the prescription fill or refill rate frequency and measure the impact in compliance and sales generated by the reminder service. The system can also measure health care savings associated with the program or any other metric available that is considered adequate.

The performance system could also estimate sales indirectly by measure the satisfaction and compliance rates through feedback coming from patient responses. Using this information, the performance system could generate reports that allow managers to monitor the service performance. The system could measure the difference in fill and refill rates of patients grouped in categories including but not limited to: disease type, channel, and demographics.

The performance measurement system may need to collect various types of data to support various performance studies. Data that might be collected includes: prescription history (when the patients filled and refilled their prescriptions); reminder service enrollment information, including the date of enrollment; a tag to classify the patient as belonging to a certain cohort or group (e.g., such a tag could be based on the medicine name, disease type, age, etc.); personal identifying information (e.g., Social Security Number, address, name, cell phone number, email address); information related to the Risk/Expense profile of the patient (e.g., high risk, high spender); brand or price of the drug the patient is using; feedback information from the patient provided through the reminder service; or when the patient's fill or refill was due.

The performance measurement subsystem also provides sponsors that are willing to pay to increase compliance a mechanism to estimate the benefits of their sponsorship. The sponsors may be willing to pay for the messages if they have a clear understanding of the benefits (e.g., margins) they are getting, and hence the possibility of financing the program (e.g., pay for the wireless messages). One possible way of measuring the impact is to encourage (by some incentive system) patients to send feedback about their compliance by responding to the messages using the feedback system described above. The analysis may be done by selecting two groups, one using the wireless reminders and another that does not.

The reminder and incentive services are ideally offered to PBM or HMO members, or members of other HC service providers, as they usually have adequate data (e.g., the refill frequency). The two groups would allow a comparison of the refill rate and the efficiency of the method, estimate the increase of sales, hospitalization cost savings and even reduction in sick day cost for companies. Moreover, the feedback channel allows patients to respond to the reminders when they take their medicines, providing data to perform detailed analysis of timing parameters when regarding compliance (e.g., time in responding to the reminder, time of day in which is more likely the patients will respond, amount of reminders successful, and even correlations between reminder success and specific drugs). The reminders may contain other types of information such as marketing (tailor made) and advertisement that may help their financing, educational contents to address part of the passive non-compliance population, or even information about other compliance programs to inform the patients about other available incentives. Finally, it also allows patients to have a feedback channel with the service providers, for example to formulate questions or give any other type of information that may help in the analysis. Note that this channel is very powerful and may help to greatly improve the result of the compliance analysis and the accuracy of the estimates obtained through it.

The following are examples of how the performance measurement subsystem may analyze information to estimate various performance metrics for the sponsors and service providers, as well as other parties. The analysis is performed using two groups, a control group and intervention group that receive reminders from the reminder service. The data analysis might show that, on average:

Group A refills 2.4 times out of a maximum of three times and group B refills 1.4 out of a maximum of three times. The price of the drug is $50, so every four months a patient generates $50 gross revenues. The cost of the messages is $0.75 per patient per month, so the total cost is $9 per year. The marginal cost of a drug Rx is $5. As a result, each patient subscribed to the system generates on average $36 of extra sales to the value chain; the drug manufacturer gets 80%; the Wholesaler gets 3%; the pharmacy gets 17% in addition to the cross-selling derived from the patient entering the store.

Chronic patients' most recent 12 month refill history is analyzed for a group of individuals. Data may be coming from refill records available at PBM or insurance databases. For each individual is known the number of refills done last year and the exact prescription price. That same group enrolls in the reminder system. One year after enrollment, the number of refills of patients prior and after the program is analyzed. For example, a patient might have refilled one time prior to enrolling in the reminder service and two times after. That patient might have been taking a $90 prescription. Thus, in one year, patient one generates $90 extra sales if subscribed to the program. The same analysis is done for all patients. Costs are deduced and the average increase in net revenues is calculated.

By introducing the use of systems that receive patient feedback, the performance management subsystem may also measure the degree of patient satisfaction and the effectiveness of the reminder system. Human or computerized intervention can be used if feedback is not within certain acceptance levels. For example, if the patient response or satisfaction with the program is below a certain level, the patient may be contacted.

Another possible intervention method may be the screening of the patient profile prior to enrollment in the program. In order to increase the patient response level and to improve the accuracy of the estimates and quality of the information gathered, tailor-made incentives and interventions can be designed depending on the patient pathology and hospitalization risk. For example, a high risk patient may be offered an economic incentive upon refill. Further analysis can be performed to correlate fill, refill, compliance, and feedback with the increase in sales of the reminder service.

Figure 5:
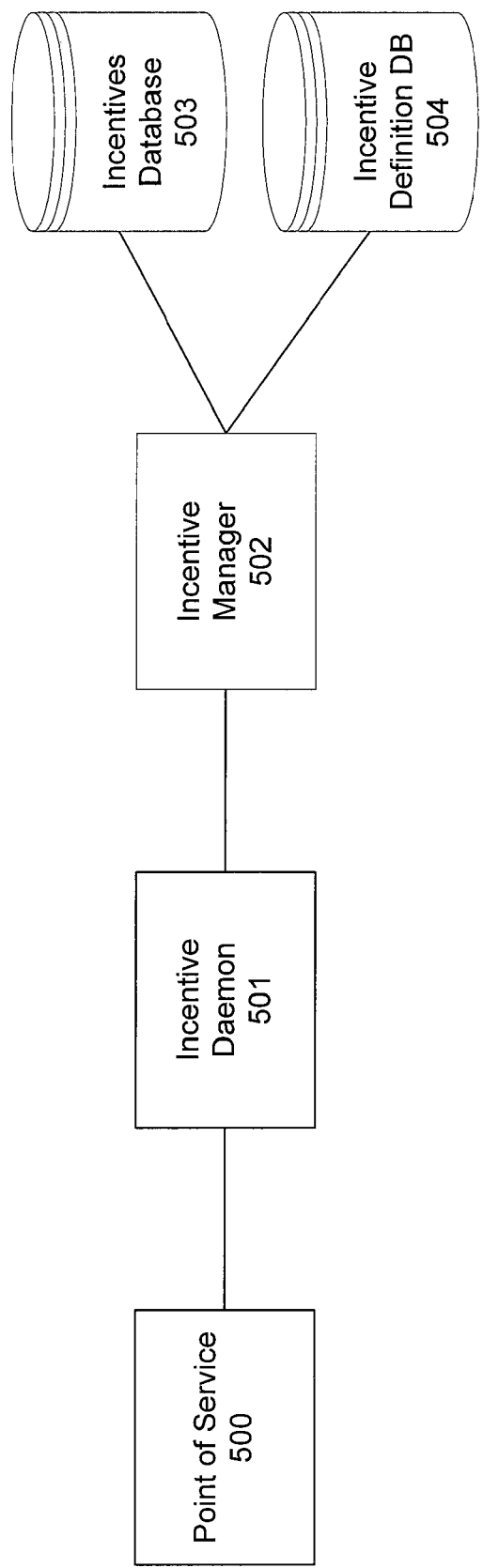
FIG. 5 illustrates the incentive subsystem in accordance with one embodiment of the present invention.

FIG. 5 illustrates the incentive subsystem in accordance with one embodiment of the present invention.

The system is capable of providing incentives to defray the costs of the alert service to the patient or to encourage adherence to a prescription drug regimen. When the point of service sets up an alert on behalf of the patient it sends incentive information (e.g., notification of successful compliance with a prescription regimen) to the Incentive Daemon 501, which activates the Incentive Manager 502 and sends it data about the alert. The Incentive Manager 502 checks the incentive eligibility for the patient or the patients' prescription and stores the relevant incentives information in the Incentive Database 503.

A number of incentives might be available upon the fulfillment of certain conditions. Incentives might be provided if a patient refills a prescription on time, replies to a reminder message, refills by mail order, refills at a particular pharmacy chain, or permits marketing material to be delivered with reminders. Incentives may include cash rebates, discounted premiums, or price discounts.

The Incentive Definitions Database 504 contains criteria defining when an incentive is awarded. These criteria may be set by the point of service, the service provider, or the sponsor. The Incentive Definitions Database 504 has a table including the fields PATIENT_ID, DAY_SET, PRESCRIPTION_ID, REFILL_NUM and TOTAL_REFILLS. PATIENT_ID and PRESCRIPTION_ID uniquely identify the patient and the prescription; DAY_SET is the day when the alert was set; REFILL_NUM is the refill order out of the total number of refills of the prescriptions, which would be the value of TOTAL_REFILLS. Whenever the Incentive Manager 502 receives a new alert, it queries the Incentive Definition Database 504 for past alerts with the same PRESCRIPTION_ID. If the patient had set a previous alert for the prescription then this refill would qualify for an incentive.

A number of criteria may be used to verify that a patient has met the conditions required to receive an incentive award. A software system may be connected to the point of sale to receive information about the prescription payment/refill, automatically update the patient profile, and trigger award/payment orders. This software system may be accessed later by authorized third parties to check which incentives are applied to certain patients and which patients fulfilled the requirements. The verification may exist in the form of a purchase ticket (that later may be sent to the sponsor) or may be stored locally in a patient card. It also may be filled by the patient via the web (connected to the service provider database) or sent via regular mail to act as a rebate (e.g., ticket and barcode from the drug container). The patient may be issued a coupon that may be used to receive discounts at the pharmacy (which later may send the coupons to the program sponsor for reimbursement). The service provider may provide the verification in acknowledgement of a feedback message sent by the patient using the above-described feedback mechanism. In such a case, the service provider will acknowledge that the patient provided feedback by providing online verification, by electronic mail, a text message, or responding to the reminders by some other channel.

Once the requirement is fulfilled there are several ways the redemption can occur. A record generated at the point of service may be sent to the service provider specifying the completion of the transaction. This record may be a computer record sent through a network to the computer system of the service provider, or the point of service may store the receipts and send them off-line in batches. When the transaction is executed, the patient is provided with the agreed award (e.g., $5 off the refill). If the point of sale requires a reimbursement (e.g., the health insurance company sponsors part of the incentive, so a pharmacy requires reimbursement of the prize to the patient) it may send a claim to the service provider/sponsor.

If the incentive is not directly related to the payment at the point of sale (e.g., $2 off the insurance premium for the next month) verification of an award can be sent from the point of service to the service provider to approve the award eligibility. The service provider can then pay the award to the patient (or ensure the award is paid) and bill the costs to the stakeholder sponsoring the incentive. If the incentive is point-based or similar, the service provider updates the patient records in the database system to reflect the award.

According to one embodiment of the present invention, incentive information is returned when an alert is set by the point of service or information about an action (e.g., refill) is received. When the refill is made, the system returns an acknowledgement message to the point of service which includes information provided by the Incentives Manager 502 about the incentive that has been rewarded. This message might instruct the point of service to provide a cash refund. According to another embodiment of the present invention, incentive information is provided to the sponsor and the sponsor provides the incentive. The service provider, in turn, would send the award information to the point of service either one-at-a-time or in a list.

The following examples show possible incentive scenarios that could be used in conjunction with the incentive subsystem described above:

The pharmacy offers over-the-shelf discounts if the patient agrees to refill at the pharmacy. The patient may see the incentive available at the service provider or by other mean (direct marketing, advertisement). The pharmacy is in charge of enrolling the patient in the system and the application is approved immediately. The pharmacy ties the incentives to opting-into the reminder system that will send reminders to the user about how to take the medication and when to refill. If the patient refills within a defined time frame the pharmacy discounts $5 in the next refill, which could be issued in the form of a coupon, ticket, or an electronic message. Note that the only sponsor is the pharmacy, so it acts as the service provider and is not required to exchange bill/reimbursement information with any other party.

The sponsor (Health Insurance company) awards the patient directly. In this case the incentive may be a reduction of the premium cost in the insurance policy of a patient if she or he complies with the prescriptions (i.e., refills on time). The sponsor here is the Health Insurance company the patient belongs to. The patient may be informed about the incentives available when buying the drug and enrolling into a patient compliance program or may be contacted by the service provider by any other means. The application is approved and the service provider database shows that the patient can get $5 back for each Lipitor refill. At refill time, the information is sent to the service provider. Then, the health insurance company would gather the information of the premium of the patient and discount the $5 from the next payment. Note that in this case the point of service only provides information about payment/refill, and the award is granted from the sponsor to the patient directly (reduction in premium cost).

The point of service (pharmacy) provides the reimbursement but the sponsor is a third party (health insurance company). This is similar to the last example, but the incentive is not a reduction in the premium but a discount on the price of the refill. The sponsor again is the health insurance company the patient belongs to, and is the one providing the incentive. The health insurance company may consider that its customer is less likely to require hospital visits or sick days if properly medicated and wants to provide an immediate reward to medication. The application process is identical to the last example. The difference in this case is that the point of service is no longer a static party just providing information but it is actually reducing the cost of the drug at the moment of the refill. In this case the information is updated in the database of the service provider that the requirement is fulfilled. Then the point of service (pharmacy) will claim a reimbursement from the sponsor directly or through its Pharmacy Benefits Manager. The sponsor may also check that the requirements are met for the patient to be awarded. Finally, the sponsor proceeds to reimburse the point of service.

Figure 6:
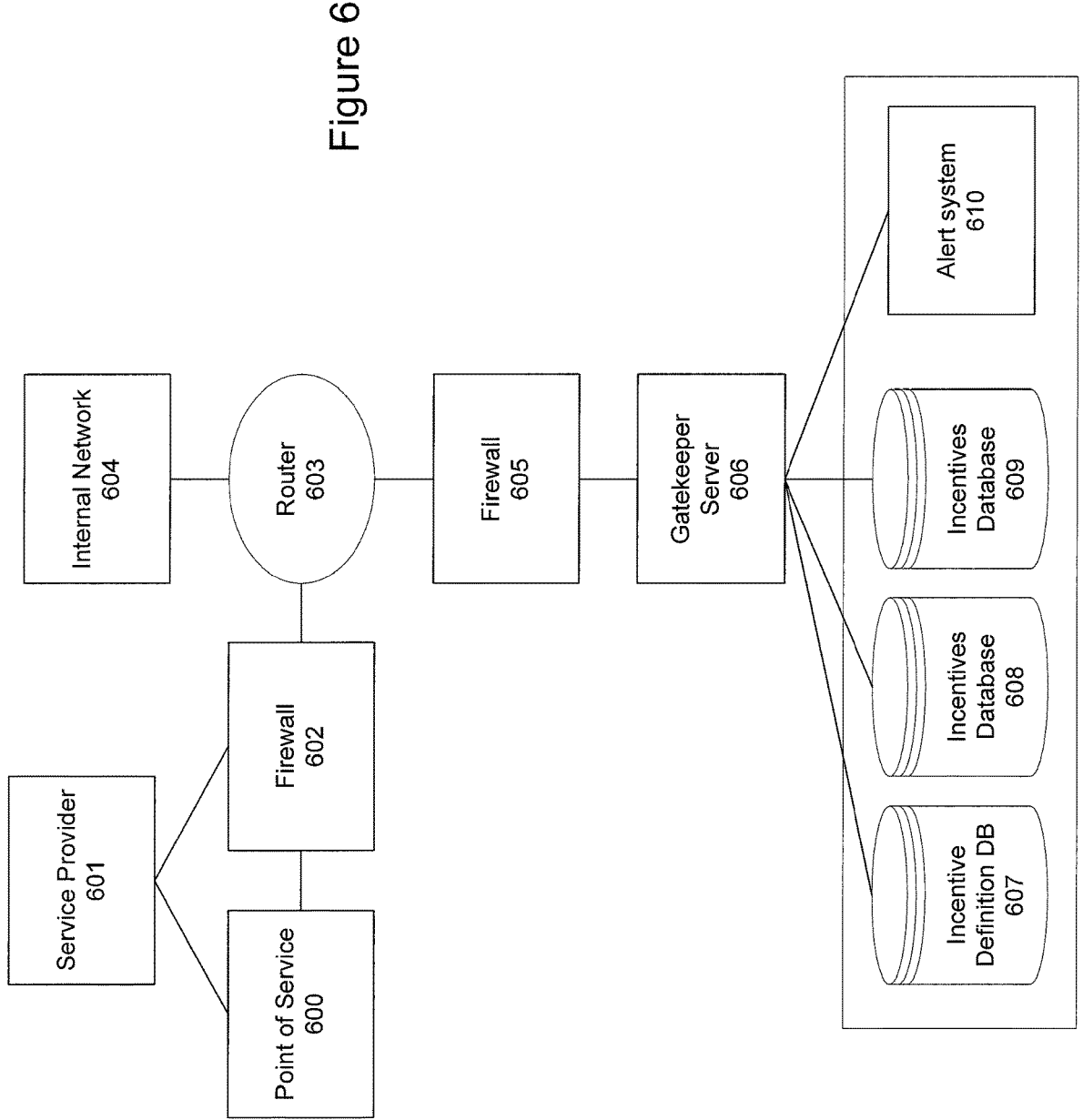
FIG. 6 illustrates the security system according to one embodiment of the present invention.

FIG. 6 illustrates the security system according to one embodiment of the present invention.

The service provider network must be secure in order to reduce the possibility that external electronic attacks would threaten the integrity or confidentiality of patient data. Since prescription data is of a very sensitive nature it is necessary to structure the network in a layered fashion where the critical applications and databases sit in the innermost layer.

Electronic messages generated at the point of service 600 or sent directly by the pharmacy benefits manager (PBM)

601 arrive at the service provider's network through a firewall 602 that forms the first barrier to electronic attacks and at the same time allows a range of authorized transactions such as web server queries and email. From there, a router 603 directs messages either to the less critical part of the internal network 604 or to the more critical second layer of the network 605.

The second layer of the network is protected by a firewall 605 which only admits messages related to the alert system. This reduces the possibility that malicious attacks can be launched against systems that have access to patient data. From the firewall 605 the message is passed to a gatekeeper server 606 that balances the load among the computers that run the different databases (e.g., 607, 608, and 609) and systems (e.g., 610). Load balancing is intended to enable easy system scalability where the increase of processing load can be distributed among a number of computers.

Figure 7:
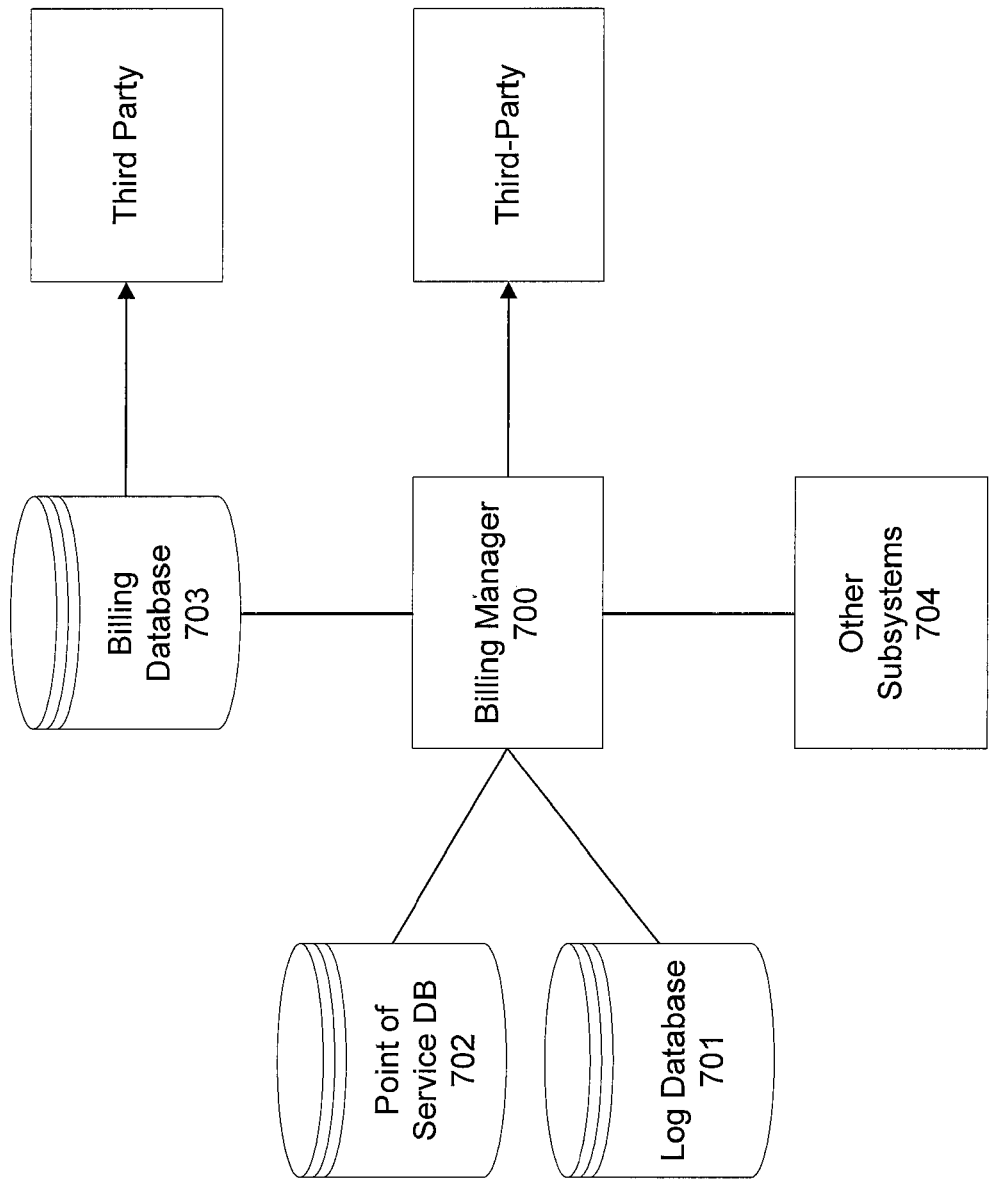
FIG. 7 illustrates the billing subsystem according to some embodiments of the present invention.

FIG. 7 illustrates the billing subsystem according to some embodiments of the present invention.

Every billing cycle, the Billing Manager 700 gathers information from about the transactions performed by each point of service from the Log Database 701 and billing information from the Point of Service Database 702. The Billing Manager 700 uses this information to generate bills which are stored in the Billing Database 703 for accounting purposes. The Billing Manager 700 may transmit these bills to the points of service or sponsors or the bills may be generated off-line by some other means. The Billing Manager 700 may also transmit billing information to other subsystems 704 such as the incentives or performance subsystems.

Figure 8:
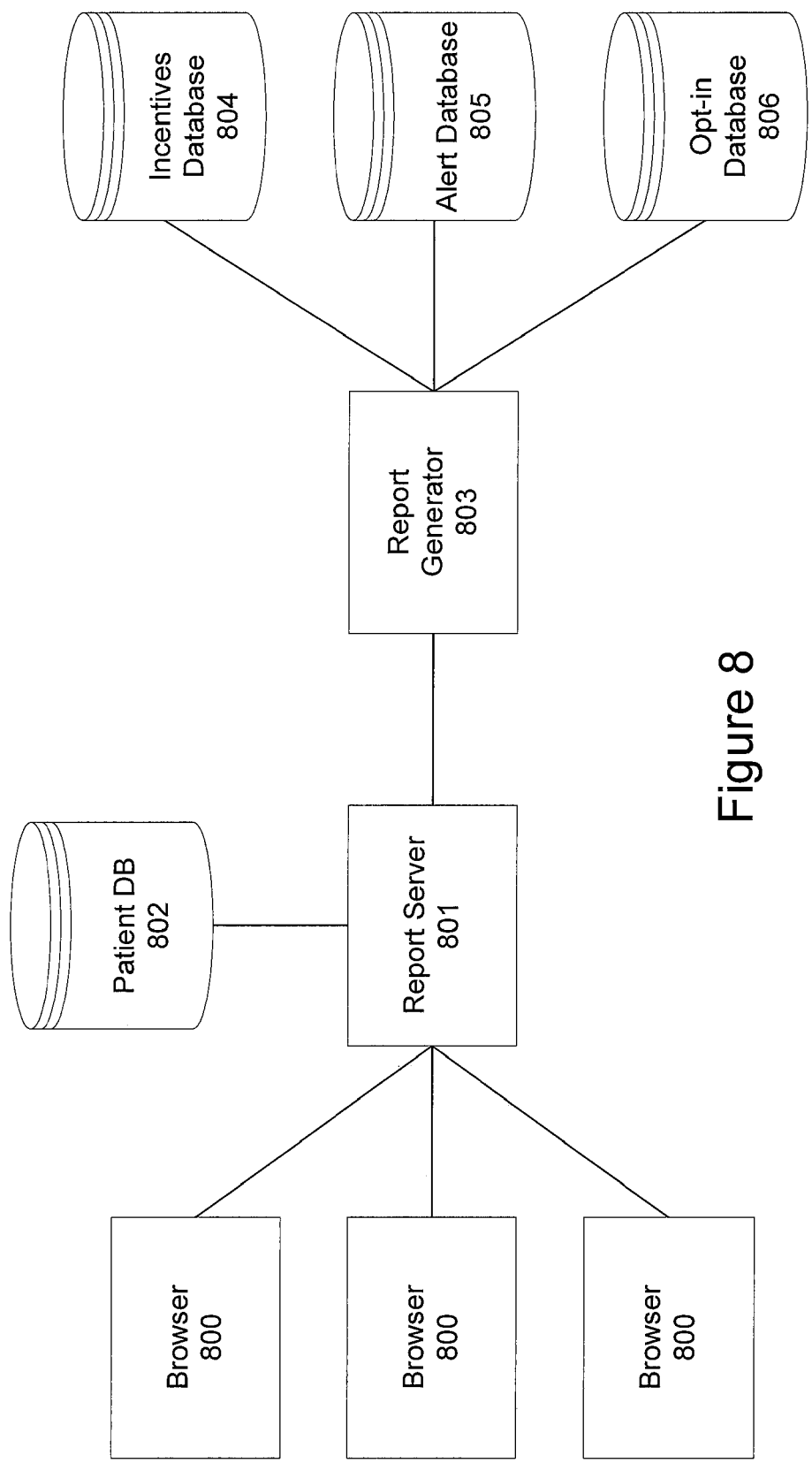
FIG. 8 illustrates the patient remote access system according to some embodiments of the present invention.

FIG. 8 illustrates the patient remote access system according to some embodiments of the present invention.

Patients are provided remote access to the alert system by the remote access subsystem. A patient may wish to access the system for a number of reasons, including to review current alerts, change the status of current alerts, review or redeem incentives, or to review opt-in information.

Patients access the system through a Browser 800, which in some embodiments may be a web browser, but may also be any other application capable of communicating with the system on a PC, PDA, or cell phone.

The Report Server 801 establishes a secure connection with the Browser and authenticates the user against information from the Patient Database 802, typically user name and password. The user name and password would be established when the patient subscribes for the service. The Report Server 801 can be a web server or any other application capable of communicating with the Browser 800 and conducting secure transactions.

Once the user has been authenticated, the Report Server 801 passes the user identity and any user queries to the Report Generator 803. Based on the user identity and user queries, the Report Generator 803 queries the Incentive Database 804, the Alert Database 805, and the Opt-in Database 806. The results of this query are used to construct a report that is returned to the Browser 800 through the Report Server 801. The report could be generated using standard tagged languages such as HTML or XML, or any language that is readable by Browser 800.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present invention as defined by the claims. Specifically, it is understood by those of skill in the art that programs and database can all be present on a single computer, distributed across multiple computers, or present in the same execution unit without changing the function and utility of the present invention.

What is claimed is:

1. A system for improving patient compliance with a prescription drug regimen, comprising:

a computer including a central processing unit;

a communications network for transmitting messages;

a patient database for storing information about a plurality of patients registered with a prescription reminder service, said information including contact information for at least one remote communications device associated with each of the plurality of patients, said contact information including a method for sending messages to the remote communications device;

an alert database for storing a plurality of prescription reminder alerts, wherein each of said plurality of prescription reminder alerts is associated with a patient and wherein each of said prescription reminder alerts includes information to determine a specific time to transmit each of said prescription reminder alerts;

an application running on said remote communication device, said application configured to retrieve information about each of said prescription reminder alerts from the alert database and to remind the patient with an alert;

an incentive definition database for storing a plurality of incentive definitions, wherein each of the plurality of incentive definitions includes an incentive event description and information about an incentive verification wherein said incentive verification is to be sent upon receipt of an event notification matching said incentive event description;

an incentive program running on said computer configured to receive an event notification, compare said event notification with the incentive event description in each of the plurality of incentive definitions in the incentive database, and to send the incentive verification to the application from each incentive definition that contains an incentive event description that matches the event notification, wherein at least one incentive definition in the incentive database contains an incentive event description that matches an event notification generated by the application in response to the application receiving information from the patient about refilling a prescription or taking prescribed drugs on schedule;

a feedback definition database for storing a plurality of feedback message templates, wherein each of the plurality of feedback message templates includes information sufficient to describe a feedback message and at least one action to be executed upon receipt of a matching feedback message; and a feedback program configured to receive a feedback message from the application on the remote communications device, to compare said feedback message to the plurality of feedback message templates in the feedback definition database, and to execute the at least one action associated with each feedback message template that matches the feedback message, wherein the at least one action includes sending a response to the feedback message, updating a preference setting associated with receiving the alert, retrieving or modifying the information of the patient in the patient database, retrieving or delivering an incentive award associated with the incentive verification, or a combination thereof.

2. The system of claim 1, wherein said alert database is distributed between the computer and the remote communication device.

3. The system of claim 1, wherein said incentive database is distributed between the computer and the remote communication device.

4. The system of claim 1, wherein said patient database is distributed between the computer and the remote communication device.

5. The system of claim 1, wherein said feedback program is distributed between the computer and the remote communication device.

6. The system of claim 1, wherein the feedback definition database is distributed between the computer and the remote communication device.

7. The system of claim 1, further comprising:
a performance database for storing information associated with a plurality of patients, including information about prescription reminder alerts sent to said plurality of patients and feedback messages received from said plurality of patients; and
a performance measurement program configured to query the performance database, wherein the query returns data from the performance database, and performs a mathematical or statistical analysis on the data returned from the performance database.

8. The system of claim 7, wherein said performance measurement program is distributed between the computer and the remote communication device.

9. The system of claim 1, wherein at least one incentive definition in the incentive database contains an incentive event description that matches an event notification generated when a specified prescription reminder alert is added to the alert database.

10. A system for improving patient compliance with a prescription drug regimen, comprising:
a computer including a central processing unit;
a communications network for transmitting messages;
a patient database for storing information about a plurality of patients registered with a prescription drug reminder service, said information including contact information for at least one remote communications device associated with each of the plurality of patients, said contact information including a method for sending messages to the remote communications device;
an alert database for storing a plurality of prescription drug reminder alerts, wherein each of said plurality of prescription drug reminder alerts is associated with a patient and wherein each of said prescription drug reminder alerts includes information to determine a specific time to transmit each of said prescription drug reminder alerts;
an application running on said remote communication device, said application configured to retrieve information about each of said prescription drug reminder alerts from the alert database and to remind the patient with an alert;
an incentive definition database for storing a plurality of incentive definitions, wherein each of the plurality of incentive definitions includes an incentive event description and information about an incentive verification wherein said incentive verification is to be sent upon receipt of an event notification matching said incentive event description; and
an incentive program running on said remote communication device configured to receive an event notification, compare said event notification with the incentive event description in each of the plurality of incentive definitions in the incentive database, and to send the incentive verification to the application from each incentive definition that contains an incentive event description that matches the event notification, wherein at least one incentive definition in the incentive database contains an incentive event description that matches an event notification generated by the application in response to the application receiving information from the patient about refilling a prescription or taking prescribed drugs on schedule, wherein the incentive verification includes a proof that the patient satisfies a criteria so as to be eligible to receive an incentive award.

11. The system of claim 10, wherein said alert database is distributed between the computer and the remote communication device.

12. The system of claim 10, wherein said incentive database is distributed between the computer and the remote communication device.

13. The system of claim 10, wherein said patient database is distributed between the computer and the remote communication device.

14. The system of claim 10, further comprising:
a feedback definition database for storing a plurality of feedback message templates, wherein each of the plurality of feedback message template includes information sufficient to describe a feedback message and at least one action to be executed upon receipt of a matching feedback message; and
a feedback program configured to compare said feedback message to the plurality of feedback message templates in the feedback definition database, and to execute the at least one action associated with each feedback template that matches the feedback message.

15. The system of claim 14, wherein said feedback program is distributed between the computer and the remote communication device.

16. The system of claim 14, wherein the feedback definition data is distributed between the computer and the remote communication device.

17. The system of claim 10, further comprising:
a performance database for storing information associated with a plurality of patients, including information about prescription reminder alerts sent to said plurality of patients and feedback messages received from said plurality of patients; and
a performance measurement program configured to query the performance database, wherein the query returns data from the performance database, and performs a mathematical or statistical analysis on the data returned from the performance database.

18. The system of claim 17, wherein said performance measurement program is distributed between the computer and the remote communication device.

19. A system for improving patient compliance with a drug regimen, comprising:
a computer including a central processing unit;
a communications network for transmitting messages;
a patient database for storing information about a plurality of patients registered with a drug reminder service, said information including contact information for at least one remote communications device associated with each of the plurality of patients, said contact information including a method for sending messages to the remote communications device;

an alert database for storing a plurality of drug reminder alerts, wherein each of said plurality of drug reminder alerts is associated with a patient and wherein each of said drug reminder alerts includes information to determine a specific time to transmit each of said drug reminder alerts;

an application running on said remote communication device, said application configured to retrieve information about each of said drug reminder alerts from the alert database and to remind the patient with an alert;

an incentive definition database for storing a plurality of incentive definitions, wherein each of the plurality of incentive definitions includes an incentive event description and information about an incentive verification wherein said incentive verification is to be sent upon receipt of an event notification matching said incentive event description;

an incentive program running on said computer configured to receive an event notification, compare said event notification with the incentive event description in each of the plurality of incentive definitions in the incentive database, and to send the incentive verification to the application from each incentive definition that contains an incentive event description that matches the event notification, wherein at least one incentive definition in the incentive database contains an incentive event description that matches an event notification generated by the application in response to the application receiving information from the patient about refilling a prescription or taking prescribed drugs on schedule;

a feedback definition database for storing a plurality of feedback message templates, wherein each of the plurality of feedback message templates includes information sufficient to describe a feedback message and at least one action to be executed upon receipt of a matching feedback message; and a feedback program configured to receive a feedback message from the application on the remote communications device, to compare said feedback message to the plurality of feedback message templates in the feedback definition database, and to execute the at least one action associated with each feedback message template that matches the feedback message, wherein the feedback message includes a response to the alert, a preference setting associated with receiving the alert, a request for reviewing or modifying the information of the patient in the patient database, a request for reviewing or redeeming an incentive award associated with the incentive verification, or a combination thereof.

20. The system of claim 19, wherein said alert database is distributed between the computer and the remote communication device.

21. The system of claim 19, wherein said incentive database is distributed between the computer and the remote communication device.

22. The system of claim 19, wherein said patient database is distributed between the computer and the remote communication device.

* * * * *